United States Patent [19]
Knodel et al.

[11] Patent Number: 5,465,895
[45] Date of Patent: Nov. 14, 1995

[54] SURGICAL STAPLER INSTRUMENT

[75] Inventors: Bryan D. Knodel, Cincinnati; Richard P. Nuchols; Warren P. Williamson, IV, both of Loveland, all of Ohio

[73] Assignee: Ethicon Endo-Surgery, Inc., Cincinnati, Ohio

[21] Appl. No.: 191,412

[22] Filed: Feb. 3, 1994

[51] Int. Cl.[6] .................................................. A61B 17/068
[52] U.S. Cl. .............................. 227/176; 227/180; 227/19
[58] Field of Search ............................... 227/19, 902, 175, 227/176, 178, 180

[56] References Cited

U.S. PATENT DOCUMENTS

| | | |
|---|---|---|
| 4,530,453 | 7/1985 | Green . |
| 4,568,009 | 2/1986 | Green . |
| 4,573,622 | 3/1986 | Green et al. . |
| 4,589,582 | 5/1986 | Bilotti . |
| 4,596,351 | 6/1986 | Fedotov et al. . |
| 4,605,001 | 8/1986 | Rothfuss et al. . |
| 4,607,636 | 8/1986 | Kula et al. . |
| 4,633,861 | 1/1987 | Chow et al. . |
| 4,633,874 | 1/1987 | Chow et al. . |
| 4,915,100 | 4/1990 | Green .................................... 227/178 |
| 4,978,049 | 12/1990 | Green . |
| 5,014,899 | 5/1991 | Presty et al. . |
| 5,040,715 | 8/1991 | Green et al. . |
| 5,156,315 | 10/1992 | Green et al. . |
| 5,156,614 | 10/1992 | Green et al. . |
| 5,170,925 | 12/1992 | Madden et al. . |
| 5,180,092 | 1/1993 | Crainich . |
| 5,263,629 | 11/1993 | Trumbull et al. . |
| 5,275,323 | 1/1994 | Schulze et al. . |
| 5,307,976 | 5/1994 | Olson et al. . |
| 5,318,221 | 7/1994 | Green et al. ............................. 227/19 |
| 5,350,400 | 9/1994 | Esposito et al. ......................... 227/902 |

FOREIGN PATENT DOCUMENTS 728848  4/1980  U.S.S.R. .

*Primary Examiner*—Scott A. Smith

[57] ABSTRACT

A surgical stapler instrument is provided for applying lateral lines of staples to tissue while cutting the tissue between those staple lines. The instrument includes a handle portion, an implement portion, a reciprocating section, a drive member and a movable actuator. The implement portion includes a staple cartridge and an anvil. The reciprocating section is adapted to move back and forth along an axis of the implement portion. The movable actuator is associated with the handle portion and is engaged with the drive member such that motion of the actuator causes the drive member to move back and forth between first and second drive positions separated by a first distance. A multiplier is further provided and is associated with the reciprocating section and the drive member for causing the reciprocating section to move back and forth between first and second reciprocating positions in response to movement of the drive member. The reciprocating section includes a work portion which, when moved distally, effects the firing of staples in the staple cartridge toward the anvil. The work portion is also provided with a reciprocating knife. The first and second reciprocating positions are separated by a second distance which differs from the first distance.

15 Claims, 16 Drawing Sheets

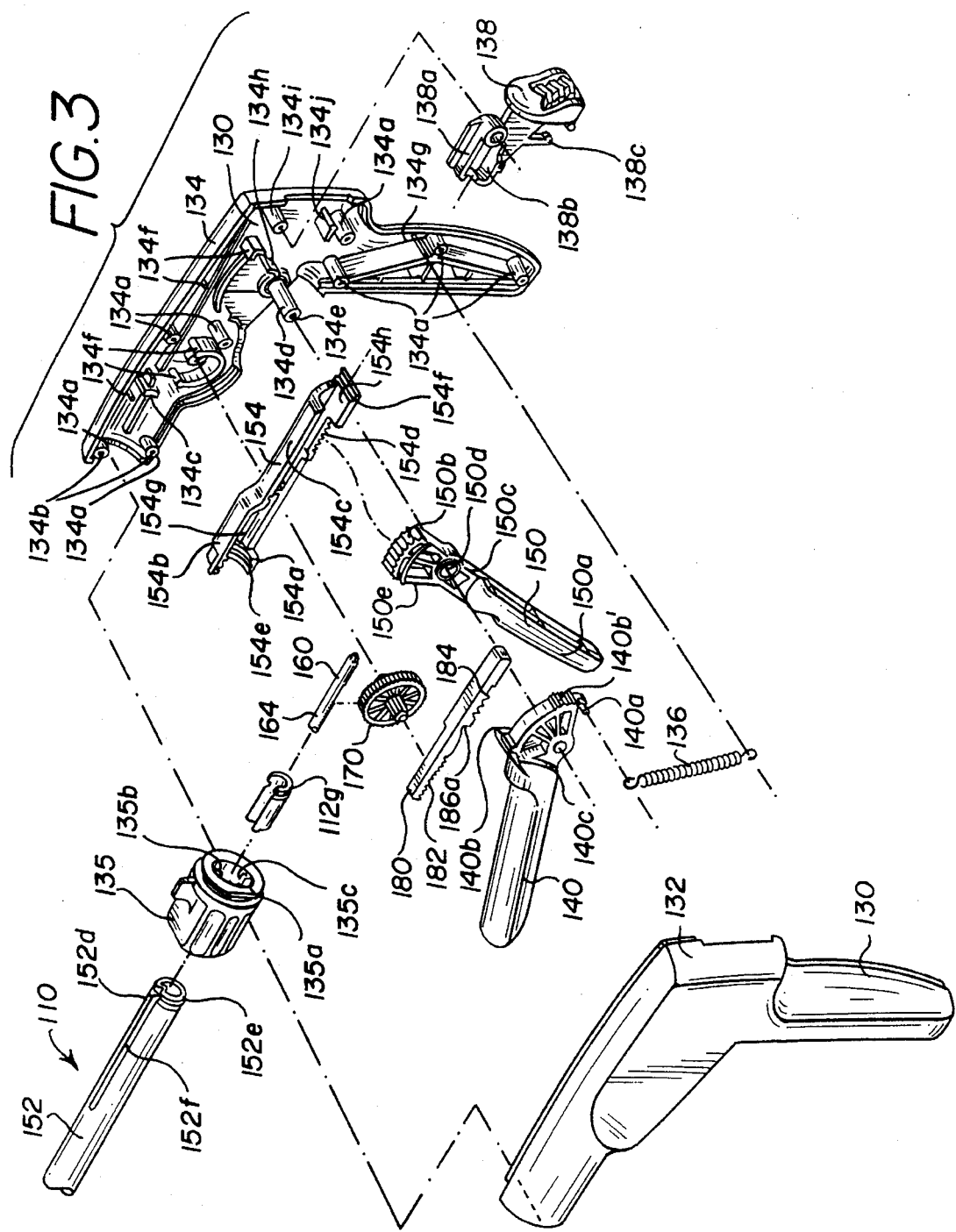

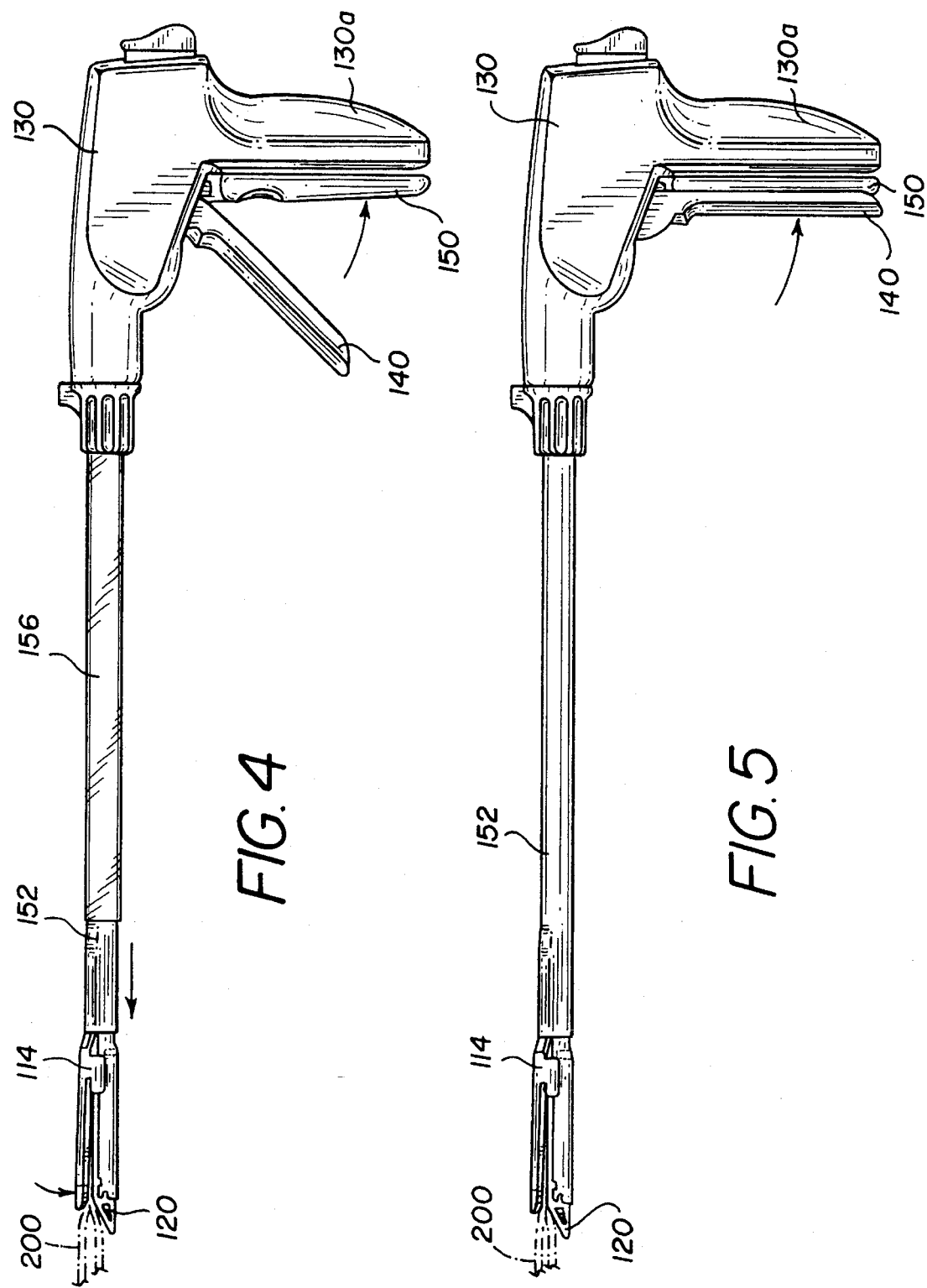

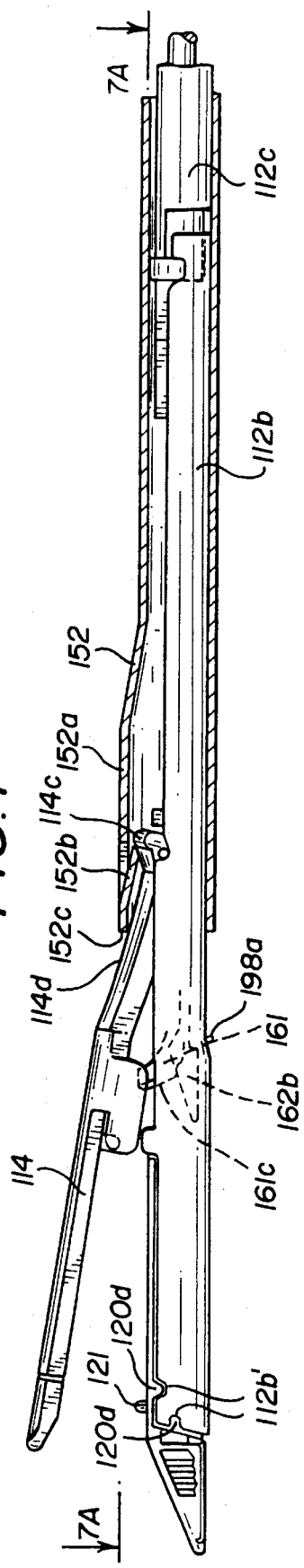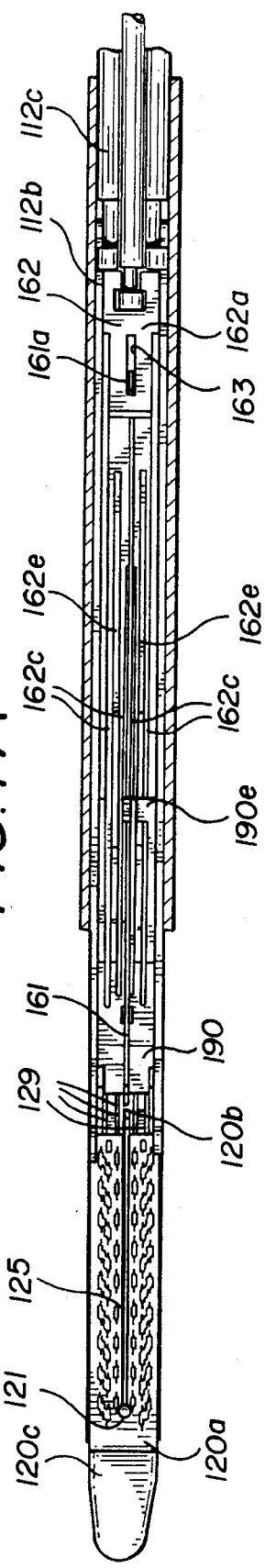

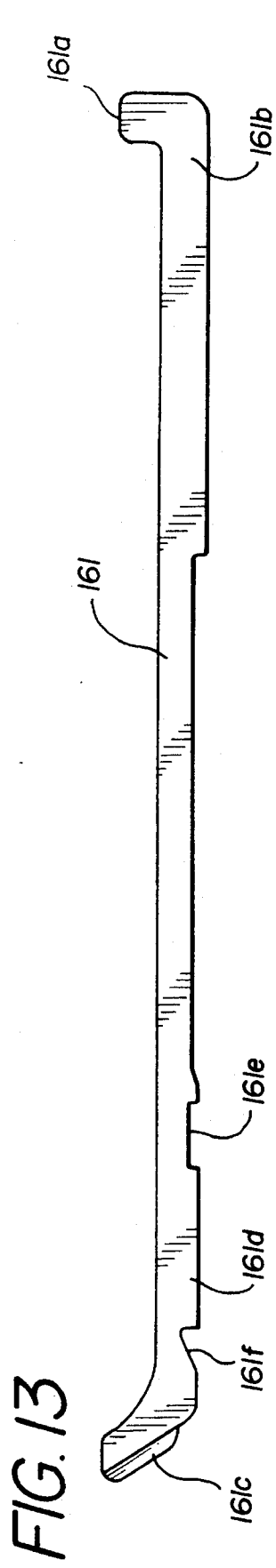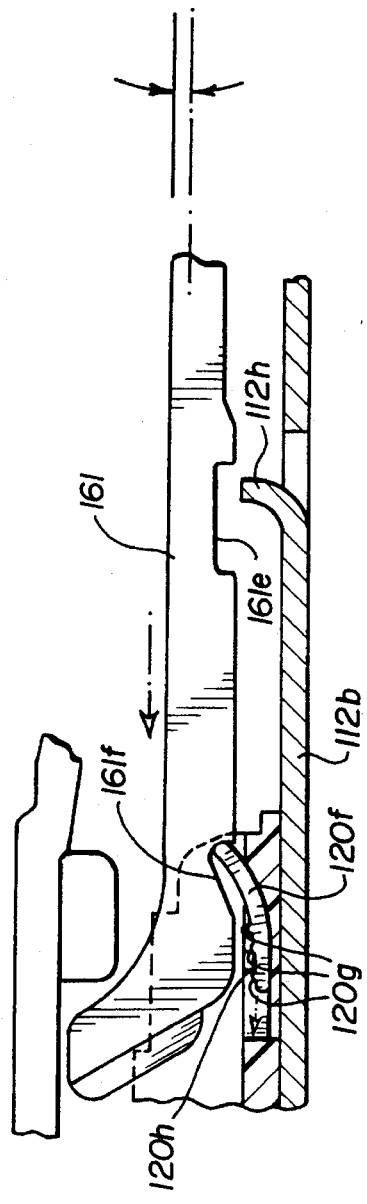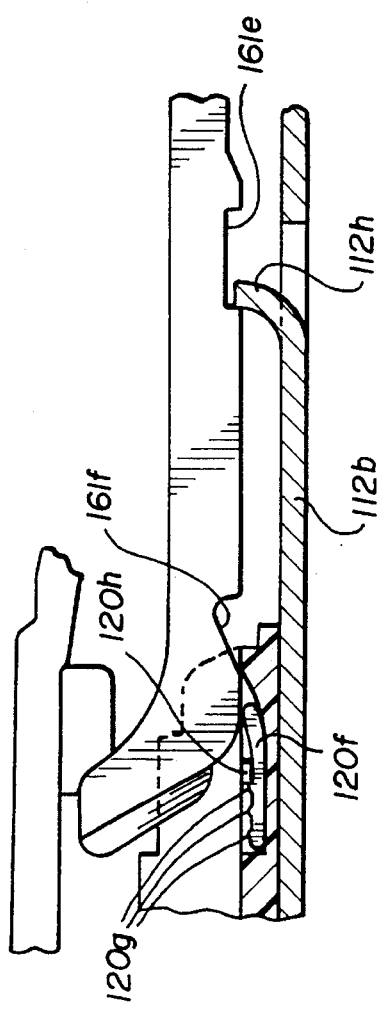

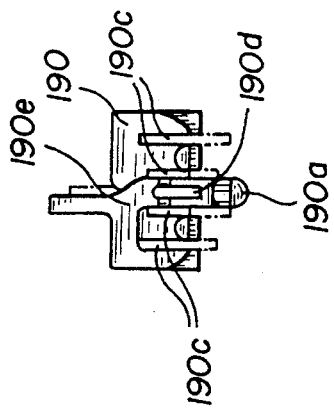
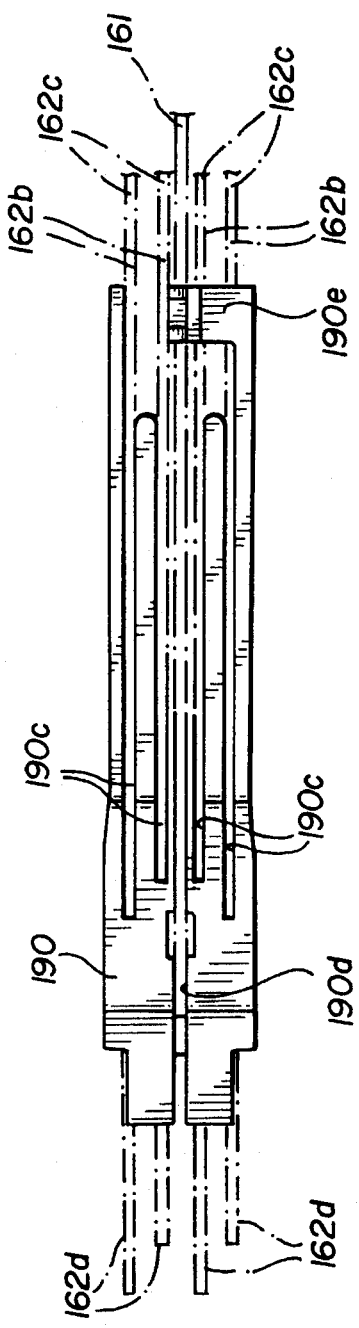
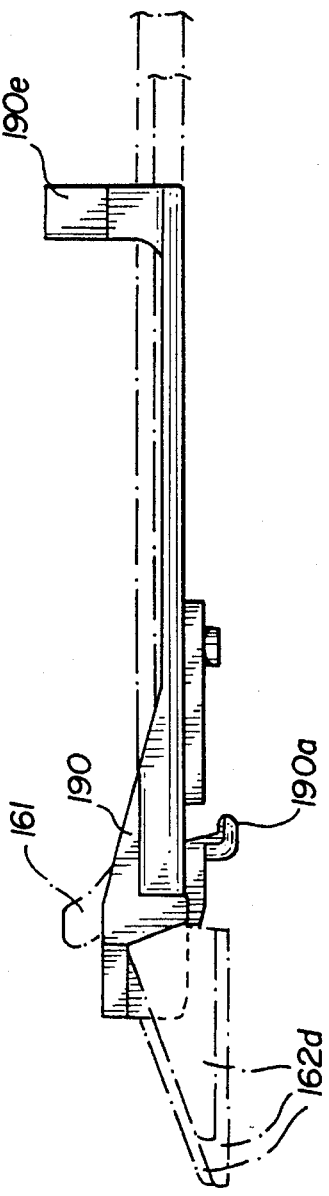

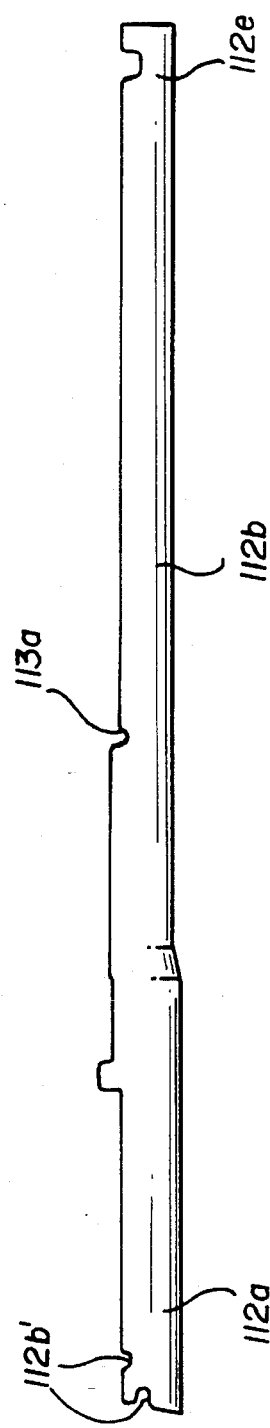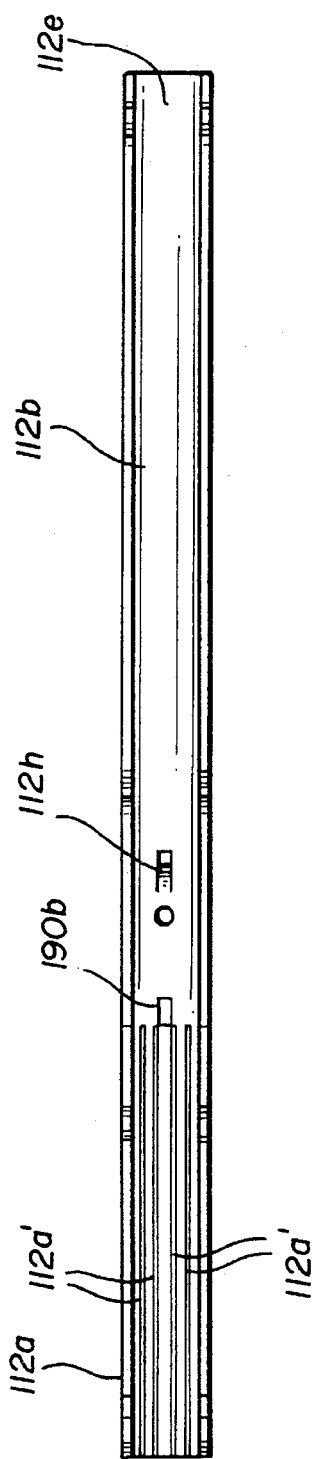
FIG. 17A
FIG. 17B

SURGICAL STAPLER INSTRUMENT

BACKGROUND OF THE INVENTION

The present invention relates in general to surgical stapler instruments which are capable of applying lines of staples to tissue while cutting the tissue between those staple lines and, more particularly, to improvements relating to stapler instruments and improvements in processes for forming various components of such stapler instruments.

Surgical staplers have been used in the prior art to simultaneously make a longitudinal incision in tissue and apply lines of staples on opposing sides of the incision. Such instruments commonly include a pair of cooperating jaw members which, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

The wedges are commonly formed from metal and assembled in a pusher block to form a single component. Since a number of individual parts must be assembled to form this component, it is costly to manufacture. Also, such components, because they are comprised of a number of individual parts, oftentimes have less than optimum stability. Further, it has been found that use of metal wedges results in a high coefficient of friction between the wedges and the drivers during staple firing.

The prior art wedges generally include a straight, single-angle cam surface. The cam surface is designed to provide sufficient force for bending over ends of the staples. While the cam design performs the desired operation, it also results in an undesirable increase in the overall length of the instrument.

Prior art mechanisms for driving wedges distally into a staple cartridge commonly include a firing mechanism and a motion transfer mechanism. The firing mechanism is engaged by a surgeon to effect staple firing. Most currently available motion transfer mechanisms, which are interposed between the firing mechanism and the pusher block, are not easily modifiable for use in stapler instruments having different staple line lengths and/or staple firing force requirements so as to permit, for a given instrument, the length of the stroke of the firing mechanism and the force required to move it to be set at ergonomically preferred values.

Accordingly, there is a need for an improved stapler instrument. Preferably, such an instrument would have wedges integrally formed as a single unit. Also, the improved stapler instrument would have wedges which are formed from an improved material such that the coefficient of friction between the wedges and the drivers during staple firing is reduced over that found in the prior art. The improved stapler would also have wedges provided with a more efficient cam surface profile. There is further a need for an improved motion transfer mechanism which is easily adaptable for use in various stapler instruments having different staple line lengths and/or staple firing force requirements so as to permit, for a given instrument, the length of the stroke of the firing mechanism and the force required to move it to be set at ergonomically preferred values.

SUMMARY OF THE INVENTION

In accordance with the present invention, an improved surgical stapler instrument is provided. The improved instrument includes a plurality of wedges and a pusher block which are integrally formed as a single wedge work member. The wedge work member is formed from a liquid crystal polymer, which material results in a reduced coefficient of friction between the wedges and the drivers during staple firing over that found in the prior art. An improved cam surface profile on the wedges is also provided. The instrument also includes a multiplier to vary the motion generated by the firing trigger to impart either increased or decreased motion to the wedges. The multiplier of the present invention is easily modifiable for use in stapler instruments having different staple line lengths and/or staple firing force requirements so as to permit, for a given instrument, the length of the stroke of the firing trigger and the force required to move it to be set at ergonomically preferred values. An improved method for forming a staple instrument anvil is also provided.

In accordance with a first aspect of the present invention, a surgical instrument is provided and comprises: a handle portion; an implement portion including first and second implements capable of performing a function during a surgical procedure; a reciprocating section adapted to move back and forth along an axis of the implement portion; a drive member; a movable actuator associated with the handle portion and engaged with the drive member such that motion of the actuator causes the drive member to move back and forth between first and second drive positions separated by a first distance; and, a multiplier associated with the reciprocating section and the drive member for causing the reciprocating section to move back and forth between first and second reciprocating positions in response to movement of the drive member. The reciprocating section includes a work portion which, when moved distally, is capable of causing the first and second implements to perform the function. The first and second reciprocating positions are separated by a second distance which differs from the first distance.

The multiplier may comprise first and second integral pinion gears. The first pinion gear is engaged with the reciprocating section and the second pinion gear is engaged with the drive member. The first pinion gear has a first diameter and the second pinion gear has a second diameter which is smaller than the first diameter. Alternatively, the first diameter of the first pinion may be smaller than the second diameter of the second pinion.

The implement portion comprises: a staple cartridge having a plurality of staples and at least one slot for receiving a distal end of the work portion; an elongated channel extending from the handle portion and having a distal end which is adapted to receive the staple cartridge; an anvil mounted on the elongated channel for pivotable movement toward and away from the cartridge; and means for effecting pivotable movement of the anvil. The staple cartridge defines the first implement. The anvil defines the second implement. The work portion causes the staples to fire toward the anvil upon movement of the distal end of the work portion into the cartridge.

The means for effecting pivotable movement of the anvil comprises: a closure tube having distal and proximal ends; a closure trigger having a handle section and a gear segment section; and, a closure yoke having distal and proximal ends. The distal end of the closure tube is adapted to engage the anvil for effecting pivotable movement of the anvil. The distal end of the yoke is connected to the proximal end of the closure tube and the proximal end of the yoke has a gear rack which is adapted to engage the gear segment section, such that movement of the closure trigger effects movement of the closure tube.

The anvil is provided with a stop and the distal end of the closure tube is provided with a tab engageable with the stop, such that movement of the closure trigger away from the handle portion causes the tab to engage the stop and pivot the anvil away from the cartridge.

The work portion comprises: a pusher block; a plurality of wedges connected to the pusher block; and a reciprocating knife. The wedges define the distal end of the work portion. The knife includes a boss at its proximal end and the pusher block is provided with a recess for receiving the boss. The recess is defined by front, rear and side surfaces formed in the pusher block. The pusher block effects movement of the knife upon engagement of the boss with one of the front and rear surfaces. Preferably, the pusher block and the plurality of wedges are integrally molded from a liquid crystal polymer.

In accordance with a second aspect of the present invention, a surgical instrument is provided and comprises: a handle portion; an implement portion having first and second implements adapted to perform a function during a surgical procedure; a reciprocating section adapted to move back and forth along an axis of the implement portion; a movable actuating mechanism associated with the handle portion; and, a multiplier engaged with the actuating mechanism and the reciprocating section such that motion of the actuating mechanism causes the multiplier to effect multiplied motion of the reciprocating section. The reciprocating section includes a work portion capable of causing the first and second implements to perform the function. The reciprocating section further includes a first drive member.

The actuating mechanism comprises a second drive member and an actuator associated with the second drive member for causing the second drive member to reciprocate back and forth between first and second drive positions.

The multiplier comprises first and second integral pinion gears. The first pinion gear is engaged with the first drive member and the second pinion gear is engaged with the second drive member. The first pinion gear has a first diameter and the second pinion gear has a second diameter which is smaller than the first diameter.

In accordance with a third aspect of the present invention, a wedge work member is provided for use in a surgical stapler having a staple cartridge provided with drivers supporting staples. The wedge work member comprises: a pusher block and a plurality of wedges formed from a liquid crystal polymer. The wedges are adapted to pass through openings in the staple cartridge to engage the drivers to effect the firing of the staples. Preferably, the wedges and the pusher block are integrally formed as a single unit. The liquid crystal polymer may comprise a fiber reinforced liquid crystal polymer. The fiber reinforced liquid crystal polymer is preferably selected from the group consisting of carbon fiber reinforced copolyesters and carbon fiber reinforced copolyester-amides.

In accordance with a fourth aspect of the present invention, a wedge work member is provided for use in a surgical stapler having a staple cartridge provided with at least one driver supporting at least one staple. The wedge work member comprises: a pusher block and at least one wedge having an elongated portion and a camming portion. The camming portion has first and second cam surfaces which sequentially engage the driver supporting the staple to effect the firing of the staple. The first cam surface forms a first angle with a first plane and the second cam surface forms a second angle with a second plane. The first plane is generally parallel with the second plane and the first angle is different from the second angle. Preferably, the first angle is greater than the second angle.

In accordance with a fifth aspect of the present invention, a method is provided for forming an anvil adapted for use in a surgical stapler. The method comprises the steps of: forming a wax pattern having an anvil shape and including a plurality of pockets therein; dipping the wax pattern into a slurry of material to form an outer shell about the wax pattern; heating the outer shell causing the wax in the outer shell to melt and leave the outer shell; filling the outer shell with molten metal to form a metal casting of the anvil within the outer shell; removing the outer shell from the metal casting; and removing surface irregularities from within each of the plurality of pockets in the casting to form a finished casting. The finished casting defines the anvil.

Accordingly, it is an object of the present invention to provide an improved surgical stapler instrument. It is further an object of the present invention to provide a wedge work member for use in a surgical stapler instrument which comprises a plurality of wedges and a pusher block which are integrally formed as a single unit. It is another object of the present invention to provide wedges for use in a stapler instrument which are formed from a liquid crystal polymer. It is still further an object of the present invention to provide wedges for use in a stapler instrument which are provided with an improved cam surface profile. It is still another object of the present invention to provide a multiplier for use in an instrument to effect multiplied motion of a work portion of the instrument. It is yet further an object of the present invention to provide an improved method for forming a surgical instrument anvil. These and other objects and advantages of the present invention will be apparent from the following description, the accompanying drawings and the appended claims.

BRIEF DESCRIPTION OF THE DRAWINGS

FIG. 3 is an exploded view showing the handle portion, the firing trigger, the closure trigger, the spring, the motion transfer mechanism, the yoke and the release button of the instrument in FIG. 1;

FIG. 4 is a side view of the instrument shown in FIG. 1 with the anvil in its tissue-clamping position;

FIG. 5 is a side view of the instrument shown in FIG. 1 with the firing trigger positioned directly adjacent to the closure trigger;

FIG. 7 is a side view, partially in cross-section, of the implement portion prior to tissue clamping;

FIG. 7a is a view taken along line 7a—7a in FIG. 7;

FIG. 8b is a view of the lower surface of the anvil shown in FIG. 8a;

FIG. 10a is a back side view of the closure trigger, the firing trigger, the spring, a portion of the yoke, a portion of the closure tube and a portion of the channel with those elements positioned as shown in FIG. 10;

FIG. 11b is a view taken along section line 11b—11b in FIG. 11a;

FIG. 13 is a side view of the knife of the instrument shown in FIG. 1;

FIG. 14a is a side view, partially in cross-section, of a portion of the staple cartridge including the lockout member and a portion of the knife;

FIG. 14b is a view similar to FIG. 14a with the lockout member pushed downward beneath a guide member of the cartridge;

FIG. 16a is a top view of the wedge guide of the instrument shown in FIG. 1;

FIG. 16b is a side view of the wedge guide shown in FIG. 16a;

FIG. 16c is an end view of the wedge guide shown in FIG. 16a;

FIG. 17a is a side view of the first channel section of the instrument shown in FIG. 1; and, FIG. 17b is a plan view of the first channel section shown in FIG. 17a.

DETAILED DESCRIPTION OF THE INVENTION

Figure 1:
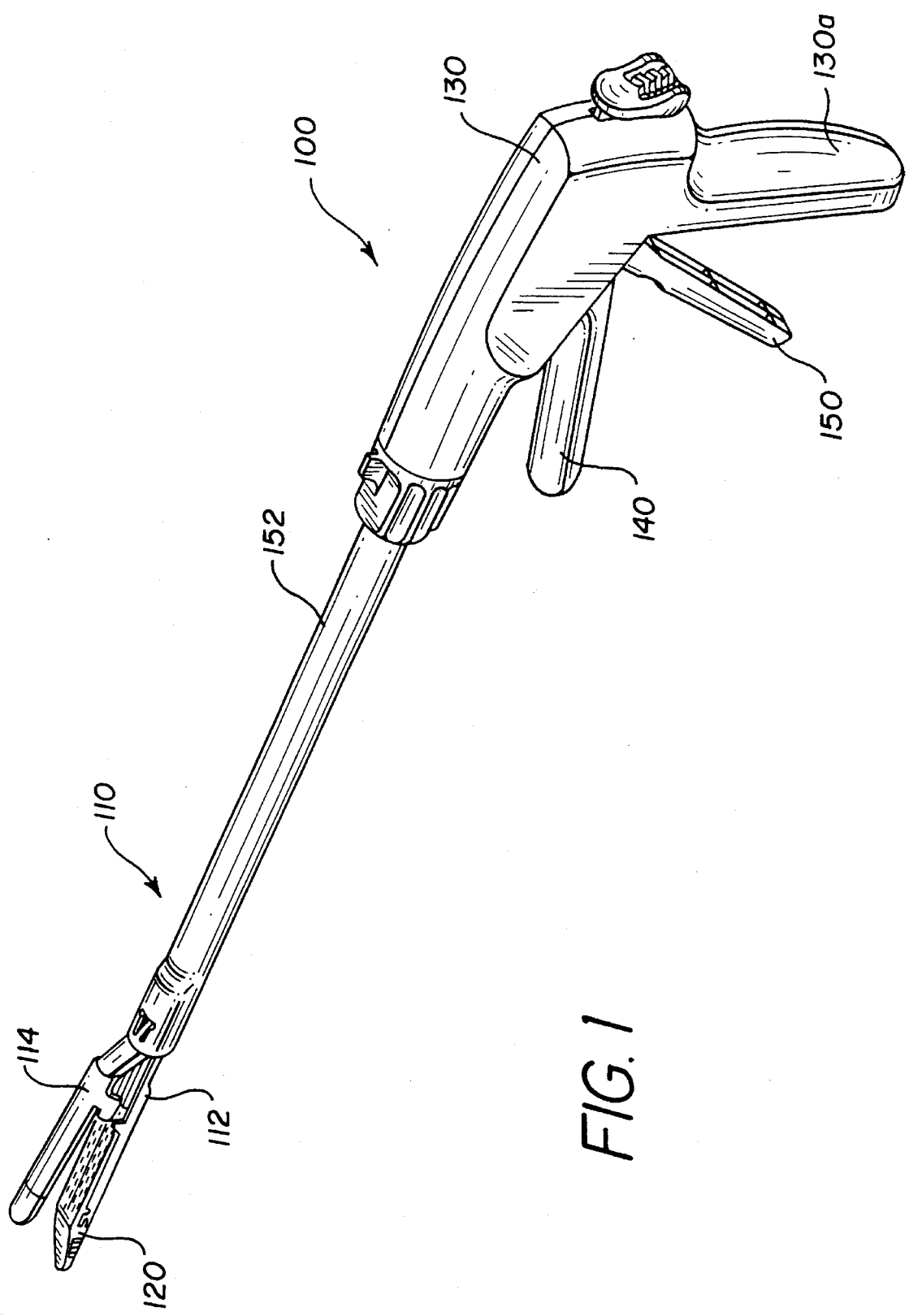
FIG. 1 is a perspective view of a surgical stapler instrument of the present invention.

Reference is now made to FIG. 1, which illustrates a surgical stapler and severing instrument 100 formed in accordance with the present invention. The stapler instrument 100 includes an implement portion 110 having an elongated channel 112 and an anvil 114, see also FIGS. 2 and 3. A distal end 112a of the elongated channel 112 releasably receives a staple cartridge 120. Housed within the staple cartridge 120 are a plurality of drivers 122a–122d, each supporting one or more staples 124, see FIGS. 11a and 11b. The anvil 114 is mounted on the channel 112 for pivotable movement toward and away from the distal end 112a of the channel 112. The instrument 100 further includes a handle portion 130, a firing trigger 140, a closure trigger 150, and a knife 161. As will be discussed more explicitly below, by grasping the closure trigger 150 and moving it to a position directly adjacent to a base section 130a of the handle portion 130, see FIG. 4, the anvil 114 is caused to pivot to a tissue-clamping position, such that it is essentially parallel to and spaced from an upper surface 120a of the staple cartridge 120. A pin 121 is provided on the cartridge 120 and is engaged by the anvil 114 when the anvil 114 is in its tissue-clamping position. After tissue clamping has occurred, the firing trigger 140 can then be moved toward the base section 130a, see FIG. 5, to cause stapling and severing of tissue 200 engaged between the anvil 114 and the staple cartridge 120.

The handle portion 130 is comprised of first and second base sections 132 and 134, see FIG. 3, which are molded from a polymeric material such as a glass-filled polycarbonate. The first section 132 is provided with a plurality of cylindrical-shaped pins (not shown). The second section 134 includes a plurality of extending members 134a, each having a hexagonal-shaped opening 134b, see also FIG. 6. The pins are received within the openings 134b and are frictionally held therein for maintaining the first and second sections 132 and 134 in assembly.

Figure 2:
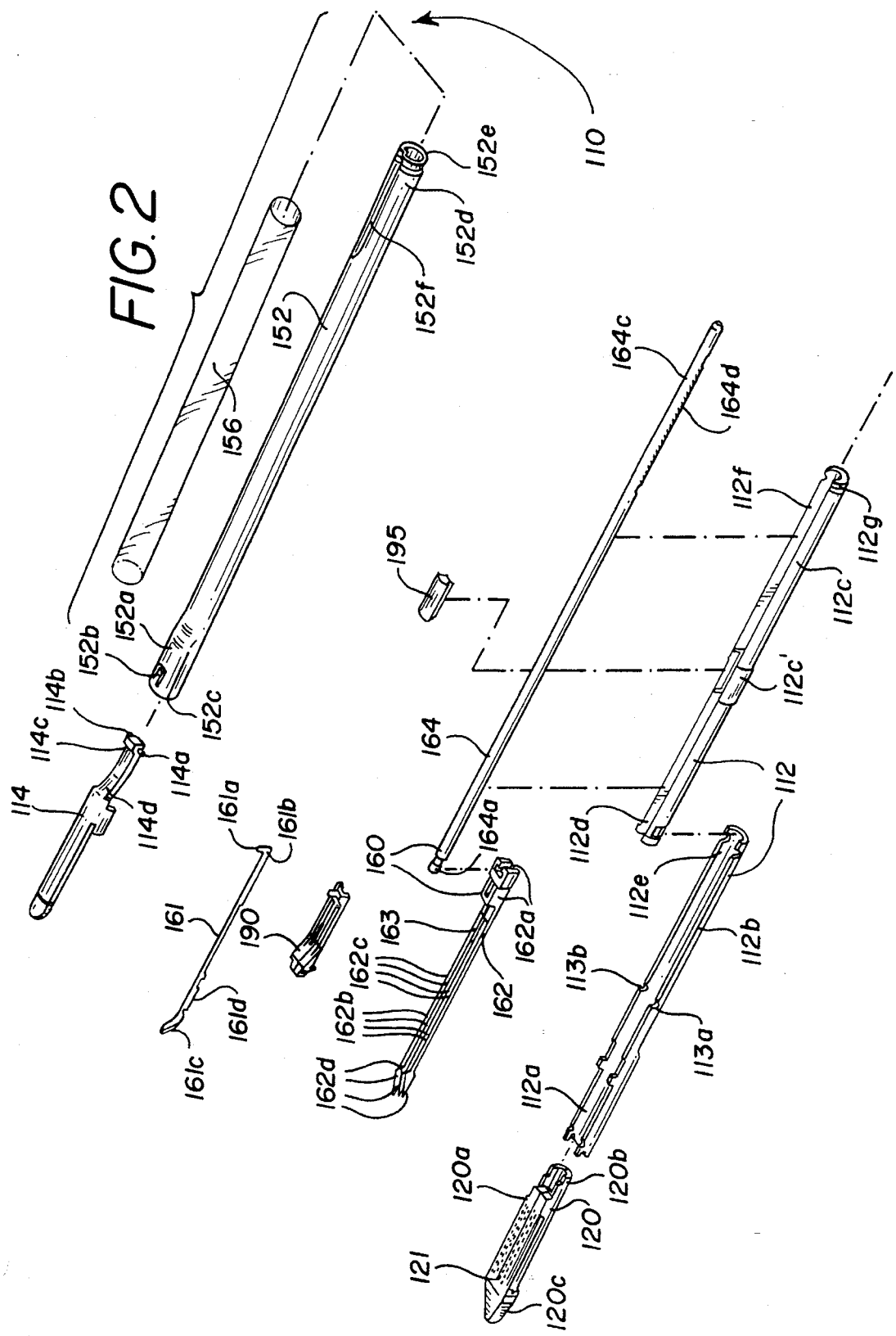
FIG. 2 is an exploded view of an implement portion of the instrument shown in FIG. 1.

The staple cartridge 120 is divided by a central, elongated slot 125 which extends from the proximal end 120b of the cartridge 120 towards its tapered outer tip 120c, see FIGS. 2 and 7a. A plurality of staple receiving pockets 126a–126f are formed within the staple cartridge 120 and are arranged in six laterally spaced longitudinal rows, see FIGS. 11a and 11b. An opening 126g extends between every two adjacent pockets 126a and 126b. An opening 126g also extends between every two adjacent pockets 126e and 126f. Positioned within the pockets 126a–126f are the staples 124.

The cartridge 120 further includes four laterally spaced longitudinal rows of staple drivers 122a–122d. Drivers 122a are slidably mounted within the pockets 126a and 126b such that each driver 122a supports two staples 124, one in a pocket 126a and one in a pocket 126b. The drivers 122b are slidably received within the pockets 126c. The drivers 122c are slidably received within the pockets 126d. Each of the drivers 122b and 122c supports a single staple 124. Each of the drivers 122b and 122c is provided with a lateral rib 123 for guiding and stabilizing the driver as it moves within its respective pocket. The drivers 122d are slidably mounted within the pockets 126e and 126f such that each driver 122d supports two staples 124, one in a pocket 126e and one in a pocket 126f.

The cartridge 120 further includes four longitudinal slots 129 extending from its proximal end 120b to its tapered outer tip 120c, see FIG. 7a. Wedges 162b provided at the distal end of a wedge work member 162 pass through the slots 129 and engage the drivers 122a–122d to effect the firing of the staples 124 toward the anvil 114, see FIG. 11b. Grooves 112a' are provided in the distal end 112a of the elongated channel 112 for receiving, guiding and stabilizing the wedges 162b as they move through the slots 129, see FIG. 17b.

As shown in FIG. 2, the elongated channel 112 is comprised of first and second channel sections 112b and 112c. In the illustrated embodiment, the first channel section 112b is formed from metal and the second section 112c is formed from a polymeric material, such as a carbon-fiber filled polycarbonate. The staple cartridge 120 is snapped in place at the distal end of the first section 112b, which end defines the distal end 112a of the elongated channel 112. Alignment tabs 120d provided on the staple cartridge 120 are received in slots 112b' in the first section 112b, see FIGS. 7 and 17a.

The distal end 112d of the second section 112c snaps onto the proximal end 112e of the first section 112b. The proximal end 112f of the second section 112c is provided with a circumferential notch 112g which is engaged by opposing channel securement members extending from the base sections 132 and 134. Only channel securement member 134c of section 134 is shown, see FIG. 3. The channel securement members extending from the base sections 132 and 134 serve to secure the channel 112 to the handle portion 130 such that the channel 112 does not move longitudinally relative to the handle portion 130.

Figure 8A:
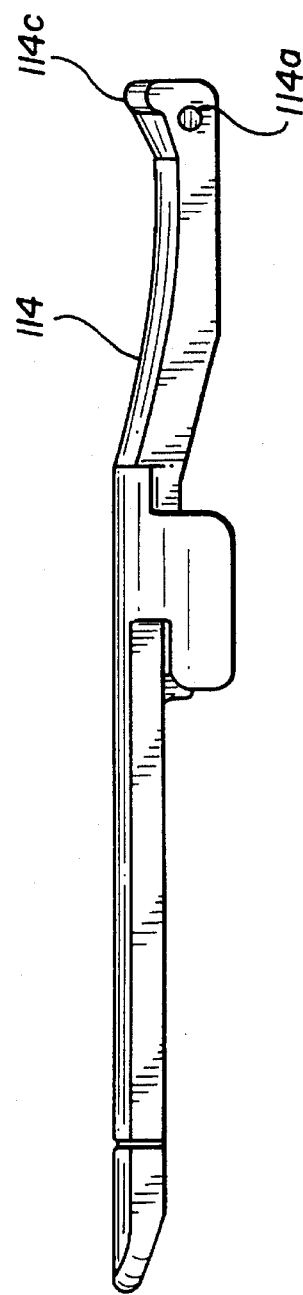
FIG. 8a is a side view of the anvil of the instrument in FIG. 1.
Figure 8B:
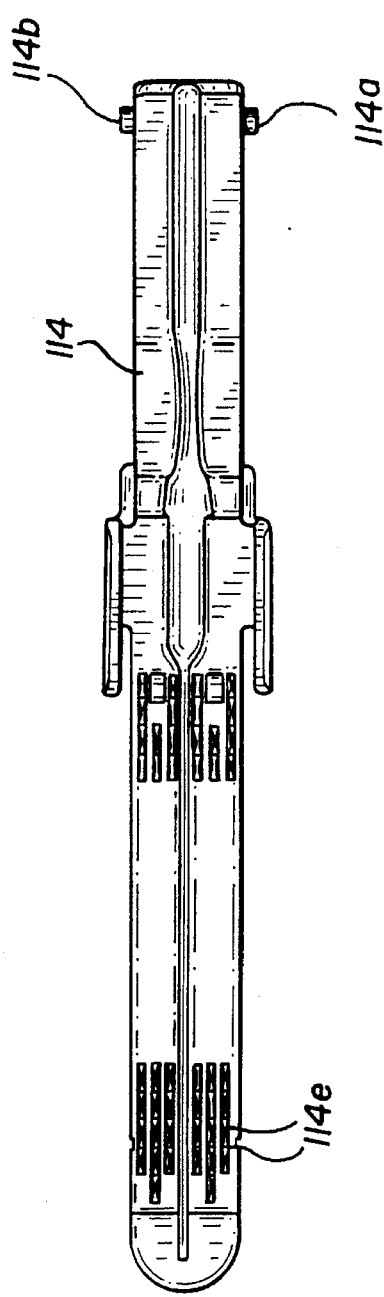

The anvil 114 includes first and second laterally positioned pins 114a and 114b, see FIGS. 2, 8A and 8B. The pins 114a and 114b are received respectively within slots 113a and 13b provided in the first channel section 112b.

Referring again to FIG. 2, a closure tube 152 is provided which moves longitudinally with respect to the handle portion 130 to effect pivotal movement of the anvil 114. The closure tube 152 has the first and second channel sections 112b and 112c extending through it. The closure tube 152 is also capable of rotating with respect to the handle portion 130 via a rotating knob 135.

The rotating knob 135 has a bore 135a extending completely through it, see FIG. 3. The knob 135 includes a protruding boss 135b extending from its inner sidewall 135c. The boss 135b is received within a slot 152f provided in the closure tube 152 such that rotation of the knob 135 effects rotation of the closure tube 152. The elongated channel 112, the cartridge 120 and the anvil 114 rotate with the closure tube 152.

An external tube 156, shown only in FIGS. 2 and 4, is received over the closure tube 152 and seals with a sealing member (not shown) provided within a trocar cannula (not shown) through which the instrument 100 passes when used during an endoscopic procedure. In the illustrated embodiment, the external tube 156 is formed from a polymeric material, such as polypropylene. The closure tube 152 is permitted to rotate with respect to the external tube 156.

Figure 9:
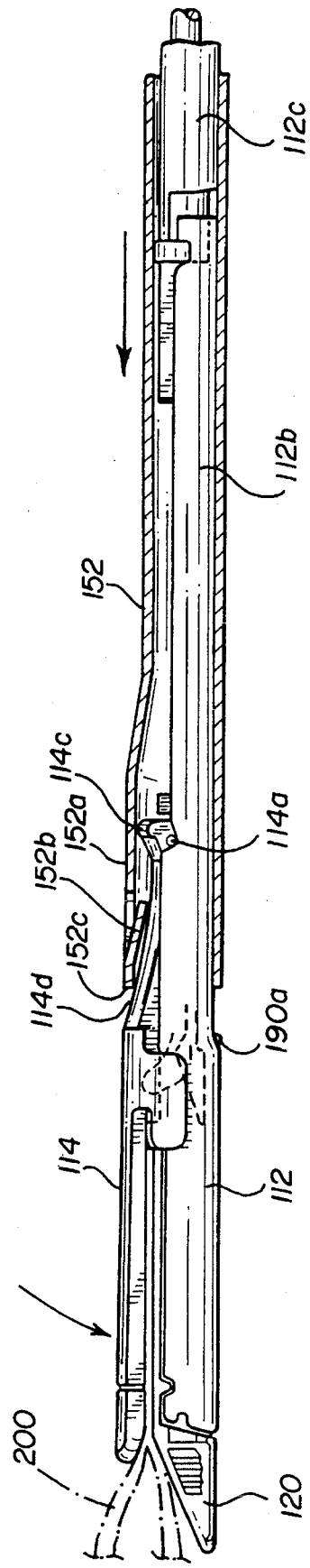
FIG. 9 is a side view, partially in cross-section, of the implement portion with the anvil shown in its tissue-clamping position.

Provided at the distal end 152a of the closure tube 152 is a tab 152b, see FIGS. 2 and 7. A stop 114c is provided at the proximal end of the anvil 114, see FIG. 8A. Upon proximal movement of the closure tube 152, the tab 152b engages the stop 114c to pivot the anvil 114 away from the distal end 112a of the channel 112, see FIG. 7. The outer distal edge 152c of the closure tube 152 defines a camming surface. When the closure tube 152 moves distally, the distal edge 152c engages an upper portion 114d of the anvil 114 causing the anvil 114 to pivot toward the distal end 112a of the channel 112 to its tissue-clamping position, see FIGS. 4 and 9.

Referring again to FIG. 3, the closure trigger 150 has a handle section 150a, a gear segment section 150b, and an intermediate section 150c. A bore 150d extends through the intermediate section 150c. A cylindrical support member 134d extending from the second base section 134 passes through the bore 150d for pivotably mounting the closure trigger 150 on the handle portion 130. A hexagonal opening 134e is provided in the support member 134d for receiving a securement pin (not shown) extending from the first base section 132. A closure yoke 154 is housed within the housing portion 130 for reciprocating movement therein and serves to transfer motion from the closure trigger 150 to the closure tube 152. Support members 134f extending from the second base section 134 and securement member 134c, which extends through a recess 154g (see also FIG. 6) in the yoke 154, support the yoke 154 within the housing portion 130.

Figure 6:
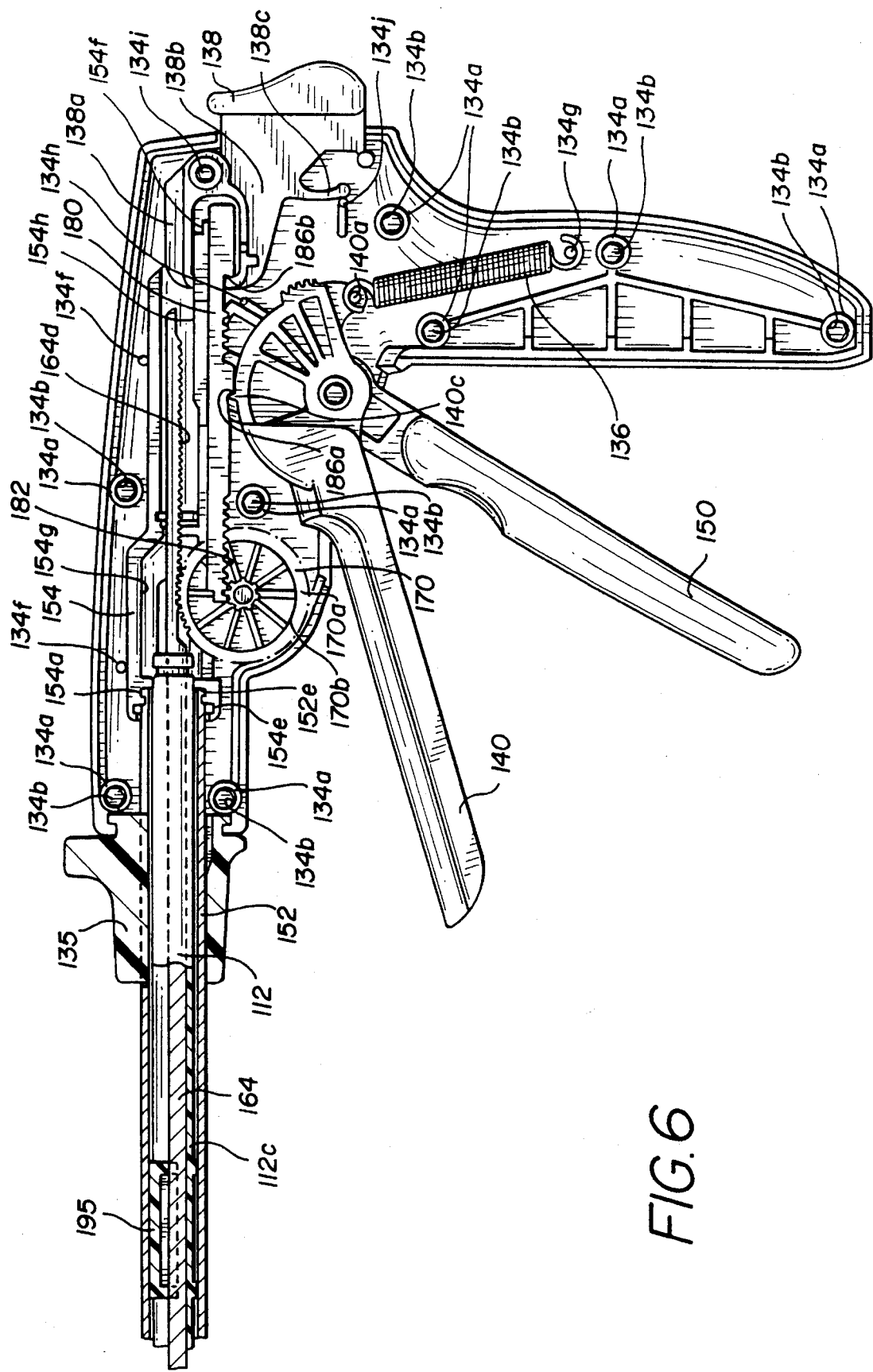
FIG. 6 is a side view, partially in cross-section, of a proximal portion of the instrument shown in FIG. 1 prior to tissue clamping.

The proximal end 152d of the closure tube 152 is provided with a flange 152e which is snap-fitted into a receiving recess 154a formed in the distal end 154b of the yoke 154, see FIGS. 3 and 6. The proximal end 154c of the yoke 154 has a gear rack 154d which is engaged by the gear segment section 150b of the closure trigger 150, see also FIG. 10a. When the closure trigger 150 is moved toward the base section 130a of the handle portion 130, the yoke 154 and, hence, the closure tube 152 move distally. Distal movement of the closure tube 152 effects pivotal movement of the anvil 114 toward the distal end 112a of the channel 112, see FIGS. 4 and 9. Movement of the closure trigger 150 away from the base section 130a effects proximal movement of the closure tube 152 causing the tab 152b on the tube 152 to engage the stop 114c on the anvil 114 and pivot the anvil 114 away from the distal end 112a of the channel 112, see FIG. 7.

The yoke 154 is provided with a second recess 154e, see FIGS. 3 and 6, which is capable of receiving a flange of a closure tube (not shown) having a size that differs from the one illustrated in FIG. 2. Thus, the yoke 154 shown in FIG. 3 can be used in the manufacture of the illustrated stapler instrument or a stapler instrument (not shown) having a closure tube with a flange of a different size.

A firing trigger return spring 136 is located within the handle portion 130. The spring 136 has opposed ends attached to a pin 134g extending from the second base section 134 and a pin 140a on the firing trigger 140. The spring 136 applies a return force to the pin 140a for biasing the firing trigger 140 in a direction away from the base section 130a of the handle portion 130.

Figure 10:
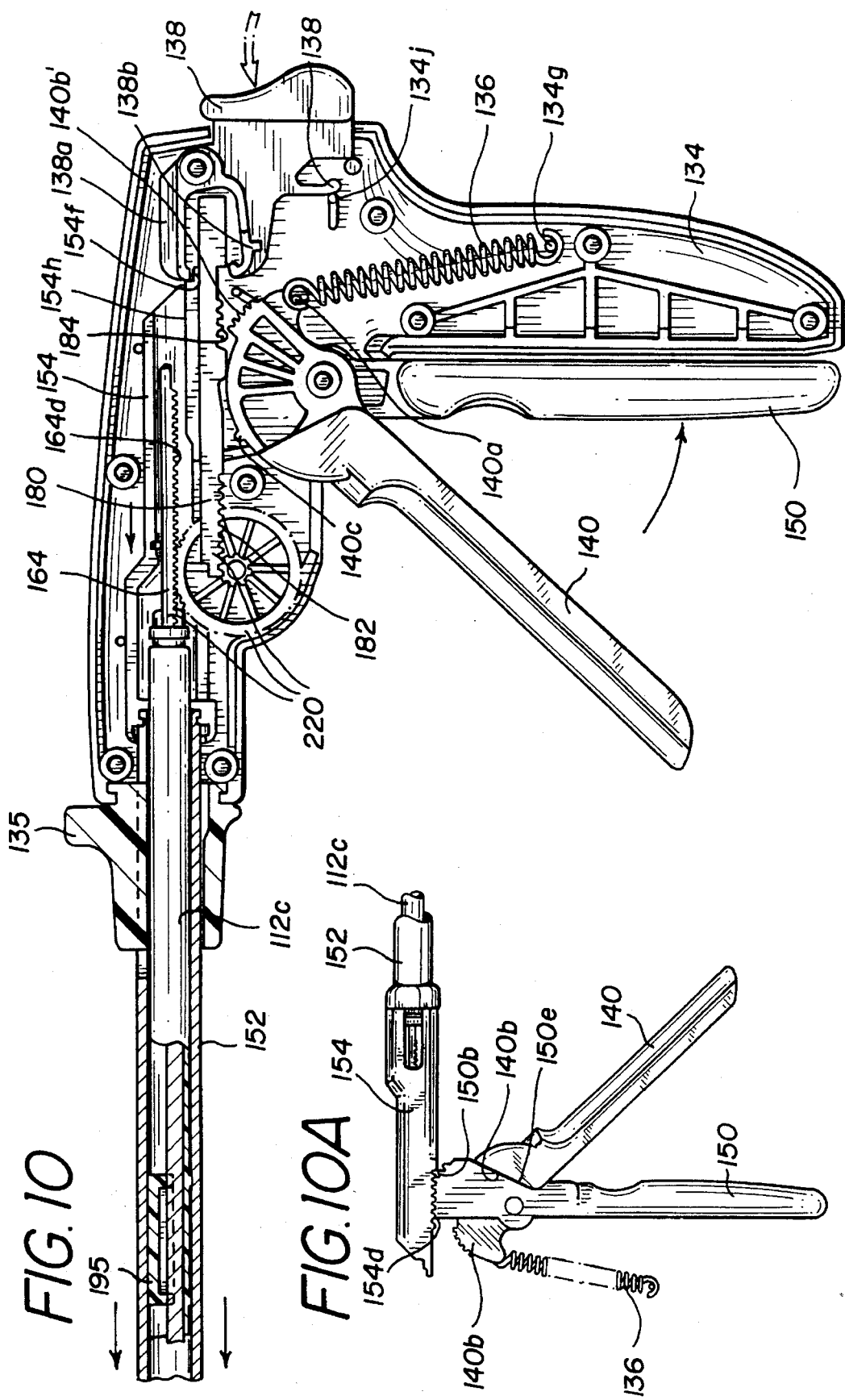
FIG. 10 is a front side view, partially in cross-section, of a proximal portion of the instrument shown in FIG. 1 with the closure trigger moved to its tissue-clamping position.

The firing trigger 140 has an engaging surface 140b which is adapted to engage with a front surface 150e on the closure trigger 150, see FIGS. 3 and 10a. As the closure trigger 150 is moved toward the base section 130a, its front surface 150e engages with the engaging surface 140b on the firing trigger 140 causing the firing trigger 140 to move to its "firing" position. When in its firing position, the firing trigger 140 is located at an angle of approximately 45° to the base section 130a, see FIGS. 4, 10 and 10a. After staple firing, the spring 136 causes the firing trigger 140 to return to its initial position, see FIGS. 1 and 6. During the return movement of the firing trigger 140, its engaging surface 140b pushes against the front surface 150e of the closure trigger 150 causing the closure trigger 150 to return to its initial position. A stop member 134h extends from the second base section 134 to prevent the closure trigger 150 from rotating beyond its initial position, see FIG. 6.

A release button 138 is pivotably mounted on extending member 134i of the second section 134 and is provided with upper and lower latch arms 138a and 138b. A spring arm 138c is also provided on the release button 138. The spring arm 138c engages with an abutment member 134j extending from the second section 134 for biasing the button 138 in a counterclockwise direction.

The proximal end 154c of the yoke 154 is provided with a receiving recess 154f, see FIGS. 3, 6 and 10. As the yoke 150 moves distally in response to proximal movement of the closure trigger 150, the upper latch arm 138a moves along an upper surface 154h on the yoke 154 until dropping into the receiving recess 154f. Once positioned in the recess 154f, the upper latch arm 138a locks the yoke 154 in its distal-most position and, hence, the anvil 114 in its tissue-clamping position. The latch arm 138a can be moved out of the recess 154f to release the anvil 114 by squeezing the closure trigger 150 while simultaneously pushing the release button 138 inward. This causes the button 138 to pivot in a clockwise direction, thereby raising the upper latch arm 138a out of the recess 154f. The yoke 154 is then permitted to move proximally in response to return movement of the closure trigger 150. As noted previously, return movement of the closure trigger 150 is caused by the engaging surface 140b on the firing trigger 140 engaging with the front surface 150e on the closure trigger 150. In the event that the force exerted by the spring 136 is not sufficient to effect the opening of the anvil 114 due to, for example, tissue being caught between the staple cartridge 120 and the anvil 114, the surgeon may manually pivot the closure trigger 150 to open the anvil 114.

The instrument 100 additionally includes a reciprocating section 160, a multiplier 170 and a drive member 180, see FIGS. 2 and 3. The reciprocating section 160 comprises the wedge work member 162 and a metal drive member 164. The distal end 164a of the drive member 164 is snap-fitted within a recess 162a provided in the proximal end of the wedge work member 162. The proximal end 164c of the drive member 164 is provided with a gear rack 164d.

Figure 12:
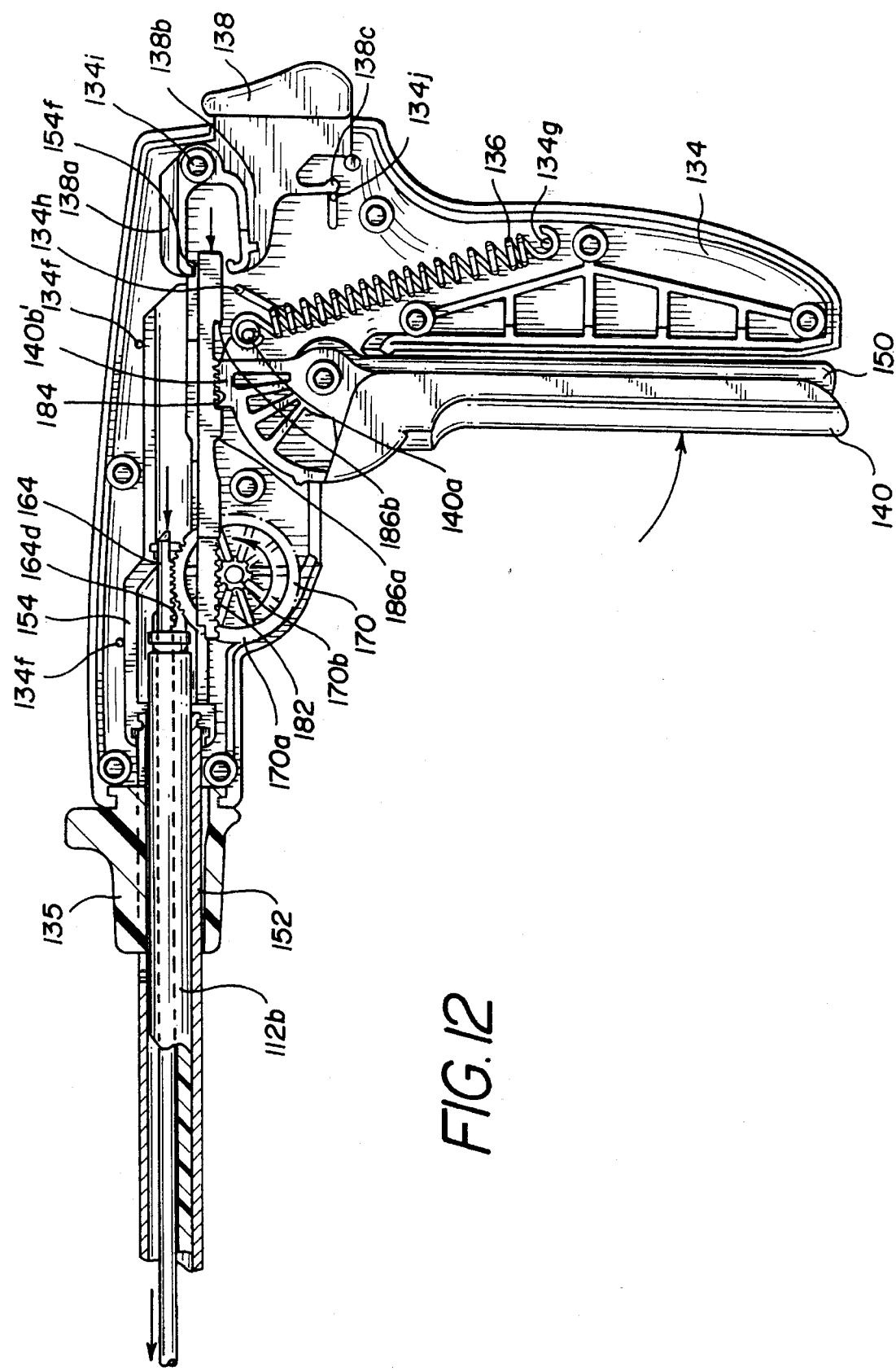
FIG. 12 is a side view, partially in cross-section, of a proximal portion of the instrument with the firing trigger shown positioned adjacent to the closure trigger.

The drive member 180 includes first and second gear racks 182 and 184, see FIGS. 3 and 12. A first notch 186a is provided on the drive member 180 intermediate the first and second gear racks 182 and 184. During return movement of the firing trigger 140, a tooth 140c on the firing trigger 140 engages with the first notch 186a for returning the drive member 180 to its initial position after staple firing, see FIG. 6. A second notch 186b is located proximal to the second gear rack 184.

The multiplier 170 comprises first and second integral pinion gears 170a and 170b, see FIGS. 6 and 12. The first pinion gear 170a is engaged with the gear rack 164d provided on the metal drive member 164. The second pinion gear 170b is engaged with the first gear rack 182 on the drive member 180. The first pinion gear 170a has a first diameter and the second pinion gear 170b has a second diameter which is smaller than the first diameter.

Figure 15A:
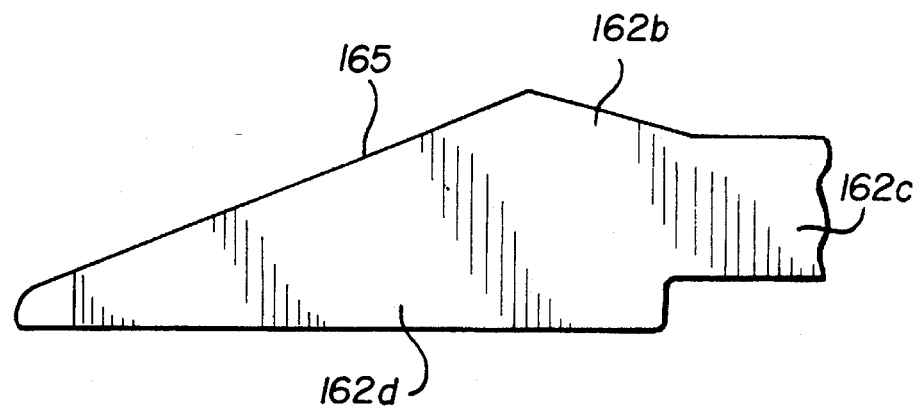
FIG. 15a is a side view of a camming portion of a wedge formed in accordance with a first embodiment of the present invention.

The wedge work member 162 comprises a pusher block 162a and four wedges 162b. Each wedge 162b comprises an elongated portion 162c and a camming portion 162d, see FIGS. 2, 7a and 15a. The camming portion 162d includes a single-angle upper cam surface 165. Upon distal movement of the wedge work member 162, the four wedges 162b enter the staple cartridge 120 through the four slots 129 such that their cam surfaces 165 engage and push upward the drivers 122a–122d in the staple cartridge 120 to effect the firing of the staples 124 toward the anvil 114.

A wedge guide 190 is seated within the first channel section 112b and acts as a guide and stabilizer for the elongated portions 162c of the wedges 162b, see FIGS. 7a and 16a–16c. The wedge guide 190 includes a locking member 190a which extends through an opening 190b (see FIGS. 11 and 17b) in the first channel section 112b for anchoring the wedge guide 190 to the first channel section 112b. The wedge guide 190 further includes four slots 190c for receiving the wedges 162b, a center slot 190d through which the knife 161 passes and a knife hold down member 190e which engages the upper surface of the knife 161.

Figure 15B:
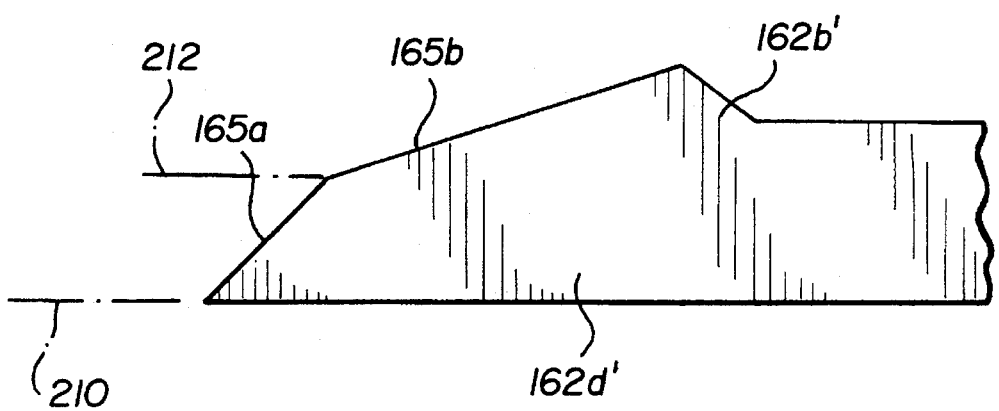
FIG. 15b is a side view of a camming portion of a wedge formed in accordance with a second embodiment of the present invention.

In accordance with a second embodiment of the present invention, the camming portion 162d' of each wedge 162b' is provided with first and second cam surfaces 165a and 165b, see FIG. 15b. The first and second cam surfaces 165a and 165b are planar in the illustrated embodiment. However, the first and second surfaces 165a and 165b may be non-planar, e.g., curvilinear. It is also contemplated that the camming portion 162d' may include more than two cam surfaces.

The first cam surface 165a forms a first angle, e.g., 25°, with a first plane 210 and the second cam surface 165b forms a second angle, e.g., 17.3° with a second plane 212. The first and second planes 210 and 212 are substantially parallel to one another. Upon distal movement of the wedges 162b', the cam surfaces 165a and 165b sequentially engage the drivers 122a–122d supporting the staples 124 to effect the firing of the staples 124. The camming portion 162d' is shorter and, hence, more efficient than the camming portion 162d. Accordingly, the instrument including wedges 162b' is shorter than the instrument 100 including wedges 162b.

Figure 11:
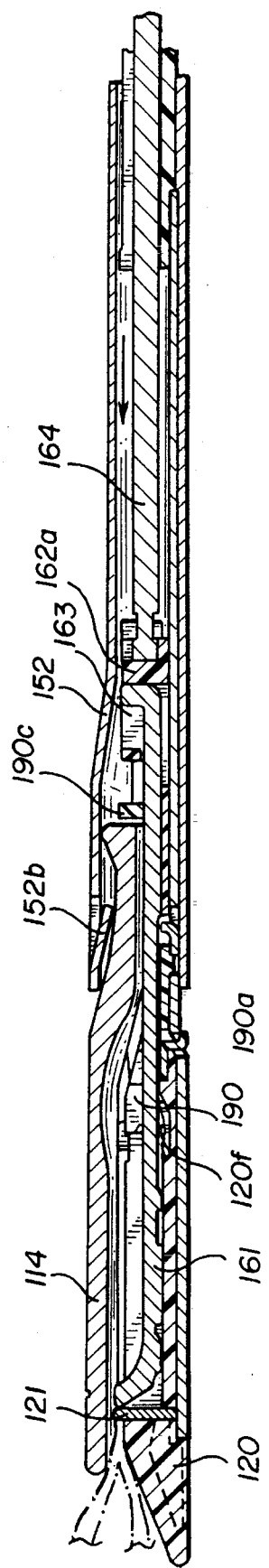
FIG. 11 is a cross-sectional view of the implement portion with the wedge work member and the knife in their distal-most positions.
Figure 11A:
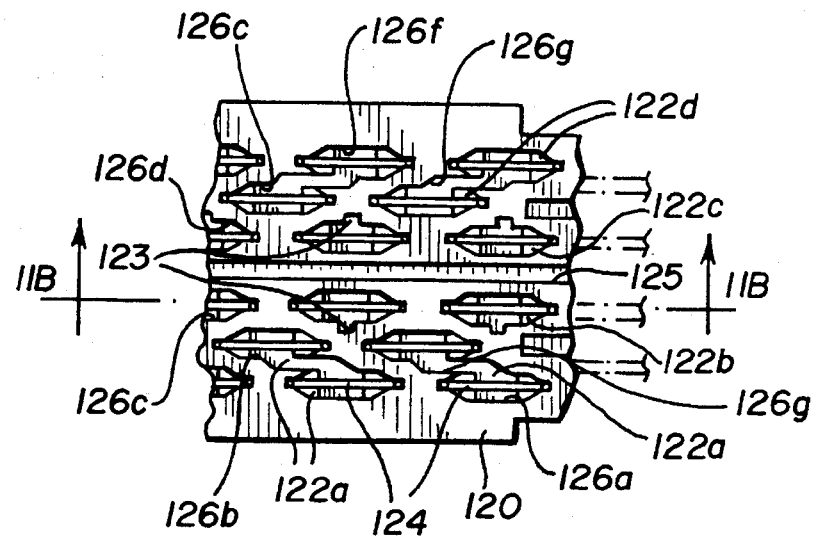
FIG. 11a is an enlarged top view of a portion of the staple cartridge of the instrument shown in FIG. 1.
Figure 11B:
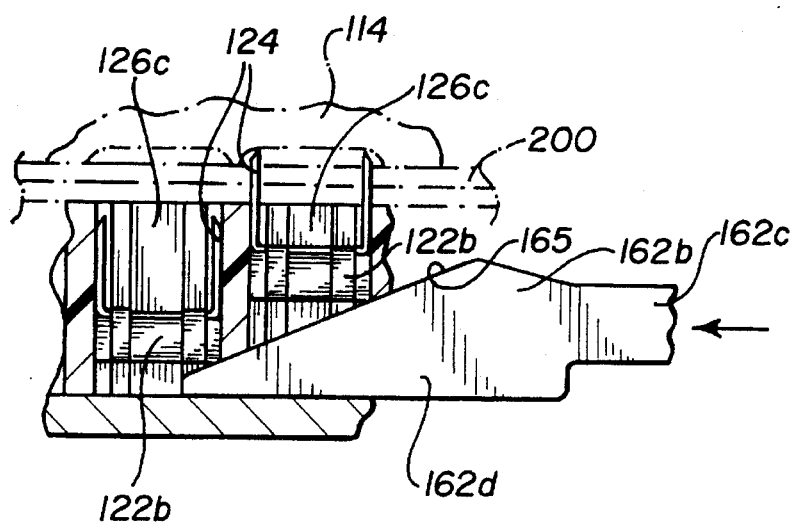

The knife 161 includes a boss 161a at its proximal end 161b and a cutting edge 161c at its distal end 161d. The pusher block 162a includes a recess 163 for receiving the boss 161a. The recess 163 is defined by front, rear and side surfaces formed in the pusher block 162a. The pusher block 162a effects movement of the knife upon engagement of the boss 161a with one of the front and rear surfaces of the pusher block 162a. In FIG. 11, the rear surface of the pusher block 162a is in engagement with the knife 161.

As shown in FIGS. 14a and 14b, the cartridge 120 includes a lockout member 120f having raised portions 120g. The lockout member 120f serves to lift the knife 161 over an upwardly extending obstruction member 112h on the first channel section 112b. This causes the obstruction member 112h to be cleared by a first notch 161e provided in the knife 161 such that the knife 161 may proceed into the slot 125 in the staple cartridge 120, see FIGS. 13 and 14a. A second notch 161f in the knife 161 moves the lockout member 120f distally beneath a guide member 120h of the cartridge 120 as the knife 161 moves distally. The proximal-most raised portion 120g engages with the guide member 120h to lock the lockout member 120f in place. After stapling and subsequent proximal movement the knife 161 to its initial position, the knife 161 cannot again move distally such that it passes through the slot 125 in the cartridge 120 since the first notch 161e cannot clear the obstruction member 112h, see FIG. 14b. Thus, refiring of the spent cartridge 120 is not possible.

Preferably, the pusher block 162a and the four wedges 162b are integrally molded from a liquid crystal polymer. Such a polymer is commercially available from Hoechst Celanese under the trademark Vectra® and may comprise a carbon fiber reinforced copolyester, sold as grade A230, or a carbon fiber reinforced copolyester-amide, sold as grade B230. To improve the stability of the four wedges 162b, stabilizing portions 162e are molded between the outer pairs of the elongated portions 162c of the wedges 162b, see FIG. 7a.

The firing trigger 140, also referred to herein as a movable actuator, is provided with a gear segment section 140b', see FIG. 3. The gear segment section 140b' engages with the second gear rack 184 on the drive member 180 such that motion of the firing trigger 140 causes the drive member 180 to move back and forth between a first drive position, shown in FIGS. 6 and 10, and a second drive position, shown in FIG. 12. In order to prevent staple firing before tissue clamping has occurred, the lower latch arm 138b on the release button 138 is engaged with the second notch 186b on the drive member 180 such that the drive member 180 is locked in its proximal-most position, see FIG. 6. When the upper latch arm 138a falls into the recess 154f, the lower latch arm 138b disengages with the second notch 186b to permit distal movement of the drive member 180, see FIG. 10.

Because the first gear rack 182 on the drive member 180 and the gear rack 164d on the metal drive member 164 are engaged with the multiplier 170, movement of the firing trigger 140 causes the metal drive member 164 and the wedge work member 162 to reciprocate between a first reciprocating position, shown in FIGS. 6, 7, 7A and 10, and a second reciprocating position, shown in FIGS. 11 and 12. Since the diameter of the first pinion gear 170a is greater than the diameter of the second pinion gear 170b, the multiplier 170 moves the reciprocating section 160 a greater distance than the drive member 180 is moved by the firing trigger 140. The diameters of the first and second pinion gears 170a and 170b may be changed to permit the length of the stroke of the firing trigger and the force required to move it to be varied.

The metal drive member 164, the multiplier 170 and the drive member 180 comprise a motion transfer mechanism 220 which acts to transfer motion from the firing trigger 140 to the wedge work member 162, see FIG. 10. Because the size of each of the pinion gears 170a and 170b may be varied, the motion transfer mechanism 220 of the present invention is easily modifiable for use in stapler instruments having different staple line lengths and/or staple firing force requirements so as to permit, for a given instrument, the length of the stroke of the firing trigger and the force required to move it to be set at ergonomically preferred values.

In an alternative embodiment (not shown), the first diameter of the first pinion is smaller than the second diameter of the second pinion. In this embodiment, the multiplier moves the reciprocating section 160 a distance which is less than the distance that the firing trigger 140 moves the drive member 180.

A seal 195 is fitted over the metal drive member 164 and engages with the second channel section 112c for preventing air from exiting the instrument 100 during an endoscopic procedure, see FIGS. 2 and 6. Additionally, the second channel section 112c is provided with a protruding portion 112c' extending about its outer surface which serves to reduce or substantially eliminate air flow between the second channel section 112c and the closure tube 152.

A summary of the operation of the instrument 100 now follows. A fully loaded cartridge 120 is snap-fitted into the distal end 112a of the channel 112. The instrument 100 is then manipulated by the surgeon such that tissue 200 to be stapled and severed is positioned between the staple cartridge 120 and the anvil 114. Next, the surgeon moves the closure trigger 150 proximally until positioned directly adjacent to the base section 130a. This movement causes the yoke 154 and the closure tube 152 to move distally. Distal movement of the closure tube 152 effects pivotal movement of the anvil 114 toward the distal end 112a of the channel 112 to effect tissue clamping, see FIGS. 4, 9, 10 and 11. Distal movement of the yoke 154 releases the lower latch arm 138b from the second notch 186b in the drive member 180 to permit subsequent distal movement of the drive member 180.

After tissue clamping has occurred, the surgeon moves the firing trigger 140 proximally until positioned directly adjacent to the closure trigger 150, see FIG. 12. This movement causes the drive member 180 to rotate the multiplier 170 which, in turn, effects distal movement of the metal drive member 164 and the wedge work member 162. Upon distal movement of the wedge work member 162, the wedges 162b enter the staple cartridge 120 through the four slots 129 such that their cam surfaces 165 engage and push upward the drivers 122a–122d in the staple cartridge 120 to effect the firing of the staples 124 toward the anvil 114. The ends of the staples 124 are bent over as a result of their engagement with the anvil 114. Distal movement of the wedge work member 162 also effects distal movement of the knife 161 such that severing of the tissue 200 occurs. The rear surface of the recess 163 in the pusher block 162a engages the knife 161 to effect its movement through the slot 125 in the staple cartridge 120.

After staple firing, the surgeon releases the tissue 200 by simultaneously squeezing the closure trigger 150 and pushing inwardly on the release button 138. This causes the release button 138 to pivot in a clockwise direction such that the upper latch arm 138a is moved out of the recess 154f. The yoke 154 is then permitted to move proximally in response to return movement of the closure trigger 150. Proximal movement of the yoke 154 effects proximal movement of the closure tube 152 causing the tab 152b on the tube 152 to engage the stop 114c on the anvil 114 and pivot the anvil 114 away from the distal end 112a of the channel 112, see FIG. 7. The spent cartridge is then discarded.

In accordance with a further aspect of the present invention, an improved method is provided for forming the anvil 114, shown in FIGS. 8a and 8b. Initially, a wax pattern is formed having an anvil shape and including a plurality of pockets. The wax pattern is approximately 10%–20% larger than the finished anvil 114. The wax pattern is dipped into a slurry of material, such as alumina, to form an outer shell about the wax pattern. The outer shell and wax are then heated until the wax is melted and leaves the outer shell. The outer shell is then hardened by firing at an elevated temperature. Thereafter, the hardened outer shell is filled with a molten metal, such as 17-4PH stainless steel in a solution heat treated condition. After the metal has cooled, the outer shell is removed from the casting.

Surface irregularities are removed from within each of the pockets in the casting to form a finished casting. This step is preferably performed by wet abrasive blasting followed by shallow coining. Wet abrasive blasting involves forcing an aqueous slurry of a very fine abrasive material, e.g., aluminum oxide, against the pockets in the casting via compressed air. Thereafter, the pockets are coined via a highly polished die or punch which acts to reduce surface roughness by cold forming metal from peaks into valleys. Additional techniques which might be employed in performing this step including electropolishing, dry abrasive blasting and/or slurry polishing. For example, the pockets may be finished by wet abrasive blasting, dry abrasive blasting or slurry polishing followed by electropolishing. Dry abrasive blasting involves forcing an abrasive material, e.g., aluminum oxide, against the pockets via compressed air. Slurry polishing involves dipping the casting into a rotating basin having, for example, water and aluminum oxide therein.

The finished anvil 114 has a plurality of staple engaging pockets 114e, each having a substantially smooth inner surface, see FIG. 8b.

Having described the invention in detail and by reference to preferred embodiments thereof, it will be apparent that modifications and variations are possible without departing from the scope of the invention defined in the appended claims.

What is claimed is:

1. A surgical instrument comprising:

a handle portion;

an implement portion having first and second implements capable of performing a function during a surgical procedure;

a reciprocating section adapted to move back and forth along an axis of said implement portion, said reciprocating section including a work portion capable of causing said first and second implements to perform said function;

a reciprocating drive member;

a movable actuator associated with said handle portion and engaged with said drive member such that motion of said actuator causes said drive member to move back and forth between first and second drive positions separated by a first distance; and, a multiplier associated with said reciprocating section and said drive member for causing said reciprocating section to move back and forth between first and second reciprocating positions in response to movement of said drive member, said first and second reciprocating positions being separated by a second distance which differs from said first distance.

2. A surgical instrument as set forth in claim 1, wherein said multiplier comprises first and second integral pinion gears, said first pinion gear being engaged with said reciprocating section and said second pinion gear being engaged with said drive member.

3. A surgical instrument as set forth in claim 2, wherein said first pinion gear has a first diameter and said second pinion gear has a second diameter which is smaller than said first diameter.

4. A surgical instrument as set forth in claim 1, wherein said implement portion comprises:

a staple cartridge having a plurality of staples and at least one slot for receiving a distal end of said work portion, said staple cartridge defining said first implement;

an elongated channel extending from said handle portion and having a distal end which is adapted to receive said staple cartridge;

an anvil mounted on said elongated channel for pivotable movement toward and away from said cartridge, said anvil defining said second implement;

means for effecting pivotable movement of said anvil; and, said work portion causing said staples to fire toward said anvil upon movement of said distal end of said work portion into said cartridge.

5. A surgical instrument as set forth in claim 4, wherein said means for effecting pivotable movement of said anvil comprises:

a closure tube having distal and proximal ends, said distal end of said closure tube being adapted to engage said anvil for effecting pivotable movement of said anvil;

a closure trigger having a handle section and a gear segment section; and, a closure yoke having distal and proximal ends, said distal end of said yoke being connected to said proximal end of said closure tube and said proximal end of said yoke having a gear rack which is adapted to engage said gear segment section such that movement of said closure trigger effects movement of said closure tube.

6. A surgical instrument as set forth in claim 5, wherein said anvil is provided with a stop and said distal end of said closure tube is provided with a tab engageable with said stop, such that movement of said closure trigger away from said handle portion causes said tab to engage said stop and pivot said anvil away from said cartridge.

7. A surgical instrument as set forth in claim 4, wherein said work portion comprises:

a pusher block;

a plurality of wedges connected to said pusher block, said wedges defining the distal end of said work portion; and a reciprocating knife.

8. A surgical instrument as set forth in claim 7, wherein said knife includes a boss at its proximal end and said pusher block is provided with a recess for receiving said boss, said recess being defined by front, rear and side surfaces formed in said pusher block, and said pusher block effecting movement of said knife upon engagement of said boss with one of said front and rear surfaces.

9. A surgical instrument as set forth in claim 7, wherein said pusher block and said plurality of wedges are integrally molded from a liquid crystal polymer.

10. A surgical instrument as set forth in claim 1, wherein said actuator comprises a spring-biased firing trigger.

11. A surgical instrument comprising:

a handle portion;

an implement portion comprising:

a staple cartridge having a plurality of staples and at least one slot for receiving a distal end of a work portion;

an elongated channel extending from said handle portion and having a distal end which is adapted to receive said staple cartridge;

an anvil mounted on said elongated channel for pivotable movement toward and away from said cartridge; and means for effecting pivotable movement of said anvil wherein said means for effecting pivotable movement of said anvil comprises:

a closure tube having distal and proximate ends, said distal end of said closure tube being adapted to engage said anvil for effecting pivotable movement of said anvil;

a closure trigger having a handle section and a gear segment section; and, a closure yoke having distal and proximal ends, said distal end of said yoke being connected to said proximal end of said closure tube and said proximal end of said yoke having a gear rack which is adapted to engage said gear segment section such that movement of said closure trigger effects movement of said closure tube;

a reciprocating section adapted to move back and forth along an axis of said implement portion, said reciprocating section including said work portion, wherein said work portion causes said staples to fire toward said anvil upon movement of said distal end of said work portion into said cartridge;

a movable actuator associated with said handle portion;

a multiplier connected to said actuating mechanism and said reciprocating section such that motion of said actuating mechanism causes said multiplier to effect multiplied motion of said reciprocating section.

12. A surgical instrument as set forth in claim 11 wherein said work portion comprises:

a pusher block;

a plurality of wedges connected to said pusher block, said wedges defining the distal end of said work portion; and a reciprocating knife.

13. A surgical instrument comprising:

a handle portion;

an implement portion comprising:

a staple cartridge having a plurality of staples and at least one slot for receiving a distal end of a work portion;

an elongated channel extending from said handle portion and having a distal end which is adapted to receive said staple cartridge;

an anvil mounted on said elongated channel for pivotable movement toward and away from said cartridge and means for effecting pivotable movement of said anvil wherein said means for effecting pivotable movement of said anvil comprises:

- a closure tube having distal and proximate ends, said distal end of said closure tube being adapted to engage said anvil for effecting pivotable movement of said anvil;
- a closure trigger having a handle section and a gear segment section; and,
- a closure yoke having distal and proximal ends, said distal end of said yoke being connected to said proximal end of said closure tube and said proximal end of said yoke having a gear rack which is adapted to engage said gear segment section such that movement of said closure trigger effects movement of said closure tube;

a reciprocating section adapted to move back and forth along an axis of said implement portion, said reciprocating section including said work portion, wherein said work portion causes said staples to fire toward said anvil upon movement of said distal end of said work portion into said cartridge; p1 a drive member;

a movable actuator associated with said handle portion and engaged with said drive member such that motion of said actuator causes said drive member to move back and forth between first and second drive positions separated by a first distance;

a multiplier associated with said reciprocating section and said drive member for causing said reciprocating section to move back and forth between first and second reciprocating positions in response to movement of said drive member, said first and second reciprocating positions being separated by a second distance which differs from said first distance.

14. A surgical instrument as set forth in claim 13, wherein said anvil is provided with a stop and said distal end of said closure tube is provided with a tab engageable with said stop, such that movement of said closure trigger away from said handle portion causes said tab to engage said stop and pivot said anvil away from said cartridge.

15. A surgical instrument comprising:

a handle portion;

an implement portion having first and second implements capable of performing a function during a surgical procedure, said implement comprising:

a staple cartridge having a plurality of staples and at least one slot for receiving a distal end of said work portion, said staple cartridge defining said first implement;

an elongated channel extending from said handle portion and having a distal end which is adapted to receive said staple cartridge;

an anvil mounted on said elongated channel for pivotable movement toward and away from said cartridge, said anvil defining said second implement;

means for effecting pivotable movement of said anvil; and, said work portion causing said staples to fire toward said anvil upon movement of said distal end of said work portion into said cartridge comprising:

a pusher block;

a plurality of wedges connected to said pusher block, said wedges defining the distal end of said work portion; wherein said pusher block and said plurality of wedges are integrally molded from a liquid crystal polymer; and a reciprocating knife;

a reciprocating section adapted to move back and forth along an axis of said implement portion, said reciprocating section including a work portion capable of causing said first and second implements to perform said function;

a reciprocating drive member;

a moveable actuator associated with said handle portion and engaged with said drive member such that motion of said actuator causes said drive member to move back and forth between first and second drive positions separated by a first distance; and, a multiplier associated with said reciprocating section and said drive member for causing said reciprocating section to move back and forth between first and second reciprocating positions in response to movement of said drive member, said first and second reciprocating positions being separated by a second distance which differs from said first distance.

* * * * *